United States Patent
Yoshikawa

(10) Patent No.: US 11,035,703 B2
(45) Date of Patent: Jun. 15, 2021

(54) SENSOR ARRANGEMENT MODE ACQUISITION DEVICE AND SENSOR ARRANGEMENT MODE ACQUISITION METHOD

(71) Applicant: Honda Motor Co.,Ltd., Tokyo (JP)

(72) Inventor: Taizo Yoshikawa, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 16/809,578

(22) Filed: Mar. 5, 2020

(65) Prior Publication Data

US 2020/0292363 A1    Sep. 17, 2020

(30) Foreign Application Priority Data

Mar. 11, 2019  (JP) .............................. JP2019-043698

(51) Int. Cl.
*G06F 11/30* (2006.01)
*G01D 18/00* (2006.01)

(52) U.S. Cl.
CPC ..................................... *G01D 18/00* (2013.01)

(58) Field of Classification Search
CPC ....................................................... G01D 18/00
See application file for complete search history.

(56) References Cited

U.S. PATENT DOCUMENTS

| | | | | |
|---|---|---|---|---|
| 2009/0140887 A1* | 6/2009 | Breed | ..................... | G01S 17/86 340/990 |
| 2020/0150695 A1* | 5/2020 | Huang | .................. | B64C 39/024 |

FOREIGN PATENT DOCUMENTS

| | | |
|---|---|---|
| CN | 103212192 | 7/2013 |
| CN | 103517789 | 1/2014 |
| CN | 105512632 | 4/2016 |
| CN | 108347709 | 7/2018 |
| JP | 2009134590 | * 6/2009 |
| JP | 2018013851 | 1/2018 |

OTHER PUBLICATIONS

Office Action of China Counterpart Application, with English translation thereof, dated Apr. 25, 2021, pp. 1-10.

* cited by examiner

*Primary Examiner* — Phuong Huynh
(74) *Attorney, Agent, or Firm* — JCIPRNET

(57) ABSTRACT

A sensor arrangement mode acquisition device capable of acquiring an arrangement mode of sensors while evaluating a detection accuracy of a predetermined action and a limitation on the number of sensors is provided. An E2PROM (13) of a sensor arrangement mode acquisition device (1) stores a database that defines a relationship between k×m correct answer ratios when the number of sensors (2) within a range of n or less is disposed in a test subject in k different arrangement modes, the k arrangement modes, and m predetermined actions. A controller (10) acquires one or more arrangement modes from the database in a case where an upper limit number of sensors, a predetermined action, and attachment areas of the sensors are selected by operating an input device (12) and a result display button (27) is pressed, and displays the acquired arrangement modes on a display (11).

13 Claims, 11 Drawing Sheets

SENSOR ARRANGEMENT MODE ACQUISITION DEVICE AND SENSOR ARRANGEMENT MODE ACQUISITION METHOD

CROSS-REFERENCE TO RELATED APPLICATION

This application claims the priority of Japan patent application serial no. 2019-043698, filed on Mar. 11, 2019. The entirety of the above-mentioned patent application is hereby incorporated by reference herein and made a part of this specification.

BACKGROUND

Technical Field

The disclosure relates to a sensor arrangement mode acquisition device that acquires a sensor arrangement mode when a predetermined action of a test subject executing a personal action is detected by a plurality of sensors.

Description of Related Art

In the related art, an action identification device disclosed in Japanese Patent Laid-Open No. 2009-134590 is known. The action identification device identifies an action of a nurse as a test subject and includes a server, an optimal database, four motion measurement devices, and the like. The four motion measurement devices are respectively mounted on both right and left arms, the chest, and the waist of the nurse. Each of the motion measurement devices is constituted by an acceleration sensor, a wireless communication device, and the like, and transmits acceleration data detected by the acceleration sensor to a server through a wireless network.

In the optimal database, acceleration data received from the acceleration sensor optimal for identifying an operation of the nurse and a sampling frequency thereof are stored as a database. In the server, an acceleration sensor to be used and a sampling frequency of acceleration data are determined from the optimal database on the basis of the position of the nurse, a feature amount is calculated when data corresponding thereto is identified, and an action of the nurse is identified using the feature amount.

Patent Documents

[Patent Document 1] Japanese Patent Laid-Open No. 2009-134590

Generally, in a case where an action of a test subject is detected using a detected signal of a sensor, it is known that detection accuracy increases as the number of sensors becomes larger. However, it may be difficult to mount sensors, sensors may not be desired to be mounted, and the number of sensors is generally limited from the viewpoint of running costs. In addition, generally, there is a demand for detecting only a predetermined action highly required to be detected, among a plurality of actions in a test subject, with a high level of accuracy. On the other hand, in the case of Japanese Patent Laid-Open No. 2009-134590, it is not possible to acquire a sensor arrangement mode that satisfies the above-described conditions and demand.

The disclosure provides a sensor arrangement mode acquisition device which is capable of acquiring a sensor arrangement mode while evaluating a detection accuracy of a predetermined action and a limitation on the number of sensors.

SUMMARY

According to an embodiment of the disclosure, there is provided a sensor arrangement mode acquisition device 1 that acquires arrangement modes of n (n is two or more) sensors (inertial measurement unit sensors 2) with respect to a test subject when m (m is two or more) predetermined actions of the test subject executing a personal action are detected. The sensor arrangement mode acquisition device 1 includes a database storage part (E2PROM 13) which stores a predetermined database defining a relationship among k×m prediction accuracy parameters (correct answer rates) indicating prediction accuracies of detection results of the m predetermined actions of the test subject when the sensors are disposed in the test subject in k (k is two or more) different arrangement modes in each of which the number of sensors within a range of n or less is disposed, the k arrangement modes of the n or less sensors, and the m predetermined actions, a number-of-sensors selection part (input device 12) for selecting a first predetermined number of sensors equal to or less than the n sensors from among the n sensors, a predetermined action selection part (input device 12) for selecting a second predetermined number of actions equal to or less than the m actions from among the m predetermined actions, and an arrangement mode acquisition part (controller 10) which acquires one or more arrangement modes according to the number of sensors within a range of the first predetermined number or less from the predetermined database associated with the second predetermined number of prediction accuracy parameters according to the second predetermined number of actions in a case where the first predetermined number of sensors is selected by the number-of-sensors selection part and the second predetermined number of actions is selected by the predetermined action selection part.

According to another embodiment, there is provided a sensor arrangement mode acquisition method of acquiring arrangement modes of n (n is two or more) sensors with respect to a test subject when m (m is two or more) predetermined actions of the test subject executing a personal action are detected. The sensor arrangement mode acquisition method includes storing a predetermined database defining a relationship among k×m prediction accuracy parameters indicating prediction accuracies of detection results of the m predetermined actions of the test subject when the sensors are disposed in the test subject in k (k is two or more) different arrangement modes in each of which the number of sensors within a range of n or less is disposed, the k arrangement modes of the n or less sensors, and the m predetermined actions, selecting a first predetermined number of sensors equal to or less than the n sensors from among the n sensors, selecting a second predetermined number of actions equal to or less than the m actions from among the m predetermined actions, and acquiring one or more arrangement modes according to the number of sensors within a range of the first predetermined number or less from the predetermined database in association with the second predetermined number of prediction accuracy parameters according to the second predetermined number of actions in a case where the first predetermined number of sensors is selected and the second predetermined number of actions is selected.

DESCRIPTION OF THE EMBODIMENTS

Hereinafter, a sensor arrangement mode acquisition device according to an embodiment of the disclosure will be described with reference to the accompanying drawings. An acquisition device 1 shown in FIG. 1 of the embodiment acquires an optimal arrangement mode of an inertial measurement unit sensor 2 when an action of a test subject such as a human is detected.

The inertial measurement part (inertial measurement unit) sensor 2 detects a three-axial (xyz-axis) acceleration, a three-axial rotation angle, and a three-axial terrestrial magnetism and outputs detected signals indicating those values.

Figure 1:
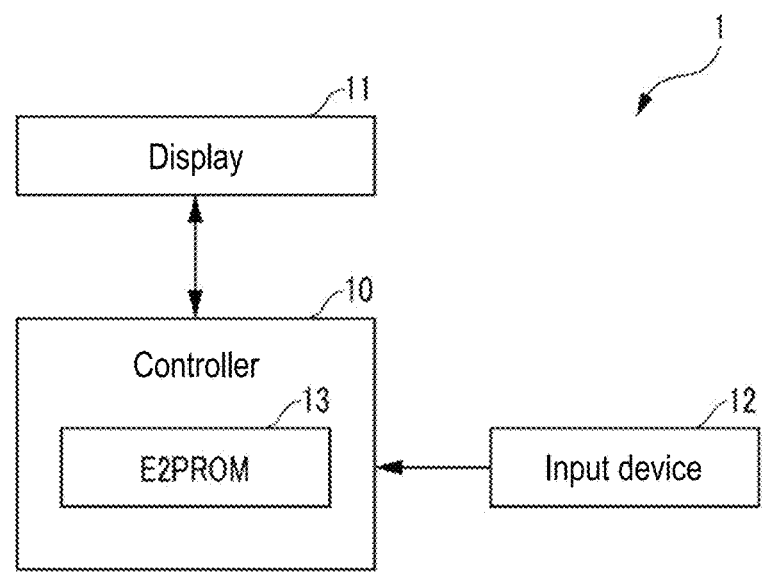
FIG. 1 is a block diagram showing a configuration of a sensor arrangement mode acquisition device according to an embodiment of the disclosure.

As shown in FIG. 1, the acquisition device 1 includes a controller 10, a display 11, and an input device 12. The controller 10 is constituted by a microcomputer including a CPU (central processing unit), a RAM (random access memory), a ROM (read only memory), a E2PROM (electrically erasable programmable read only memory) 13, an I/O interface (input/output interface), various electrical circuits (components other than the E2PROM 13 are not shown in the drawing), and the like. Various programs for executing an arrangement mode acquisition display process and the like to be described later are stored in the ROM.

Meanwhile, in the embodiment, the controller 10 is equivalent to an arrangement mode acquisition part, the display 11 is equivalent to an arrangement mode display part, the input device 12 is equivalent to a number-of-sensors selection part, a predetermined action selection part, a segment selection part, and an arrangement mode selection part, and the E2PROM 13 is equivalent to a database storage part.

In addition, a first database and a second database are stored in the E2PROM 13. The controller 10 retrieves the first database and the second database stored in the E2PROM 13 in the arrangement mode acquisition display process to be described later, and displays retrieval results on the display 11 (see FIGS. 12 and 13 to be described later). The first database and the second database will be described later in detail.

Figure 11:
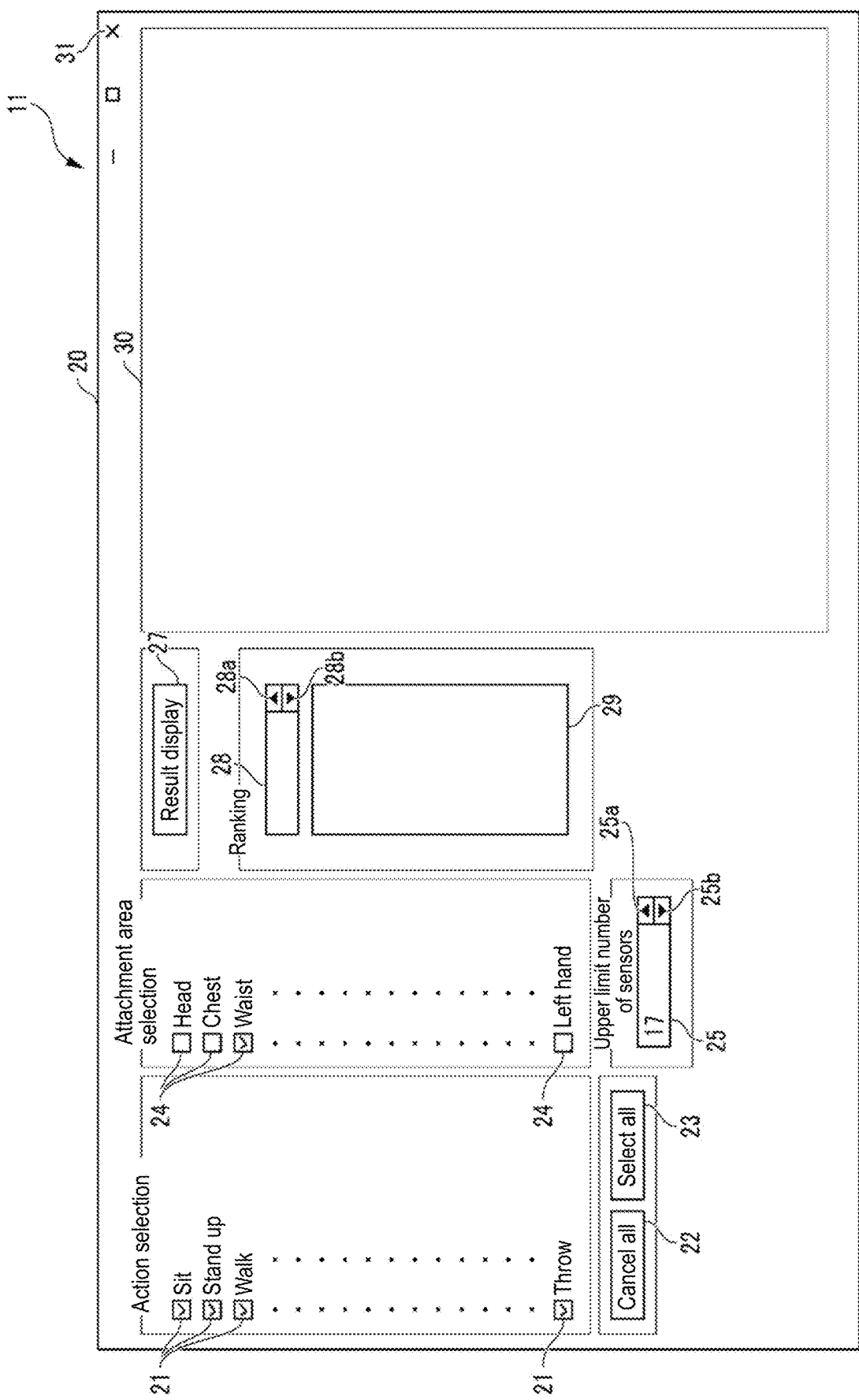
FIG. 11 is a diagram showing a display example of a selection screen.

In addition, the display 11 is electrically connected to the controller 10 and displays a selection screen 20 for acquiring an arrangement mode, and the like on the basis of a display signal received from the controller 10 in the arrangement mode acquisition display process to be described later (see FIG. 11 to be described later).

Further, the input device 12 is constituted by a keyboard and a mouse and is electrically connected to the controller 10. In the arrangement mode acquisition display process to be described later, an upper limit number of sensors, an attachment area, or the like of the inertial measurement unit sensor 2 is selected by a user operating the input device 12.

Next, the above-described first database and second database will be described. Each of the first database and the second database defines a relationship between an arrangement mode of the inertial measurement unit sensors 2, a predetermined action of a test subject, and a correct answer ratio to be described later. The first database is created using raw data to be described later, and the second database is created using arithmetic data to be described later. Meanwhile, in the following description, the first database and the second database will be collectively referred to as a "database" as appropriate.

In the case of the database, as the arrangement mode of the inertial measurement unit sensors 2, k (k is several hundreds) arrangement modes from a first pattern to a k-th pattern to be described later are set. In addition, as the predetermined action of the test subject, m (m is several tens) predetermined actions from a first action to an m-th action to be described later are set.

In addition, the correct answer ratio indicates a rate at which it is predicted that the m predetermined actions from the first action to the m-th action can be accurately detected when the test subject executes the m predetermined actions in a case where the inertial measurement unit sensors 2 are disposed in the test subject with any pattern in the first to k-th patterns, and the correct answer ratio is set as described below. Meanwhile, in the embodiment, the correct answer ratio is equivalent to a prediction accuracy parameter.

Next, a database creating method will be described. In the creating method, 17 inertial measurement unit sensors 2 are electrically connected to the controller 10 mentioned above, and a database is created by the controller 10 as described below using sampling data of detected signals of the 17 inertial measurement unit sensors 2.

Figure 2:
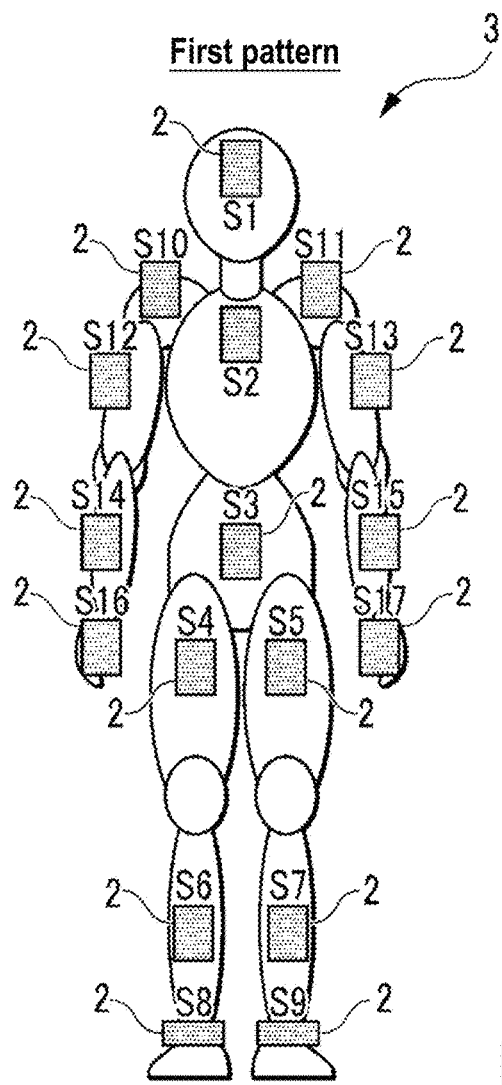
FIG. 2 is a diagram showing a first pattern of an arrangement mode of inertial measurement unit sensors.

First, as shown in FIG. 2, the body of a test subject 3 (person) is divided into a total of 17 segments S1 to S17 of a head S1, a chest S2, a waist S3, and a left hand S17. Subsequently, as shown in the drawing, a mode in which one inertial measurement unit sensor 2 is actually disposed at each of the areas of the 17 segments S1 to S17 is set as a first pattern of an arrangement mode of the inertial measurement unit sensors 2. Meanwhile, in the following description, an arrangement mode of the inertial measurement unit sensors 2 will be referred to as an "arrangement mode" as appropriate.

Figure 3:
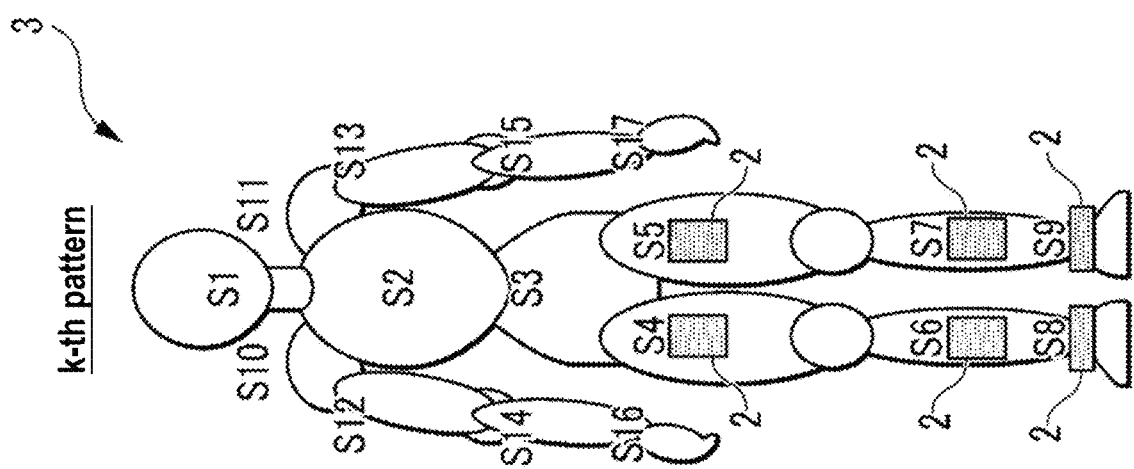
FIG. 3 is a diagram showing second to k-th patterns in an arrangement mode of inertial measurement unit sensors.
Figure 3:
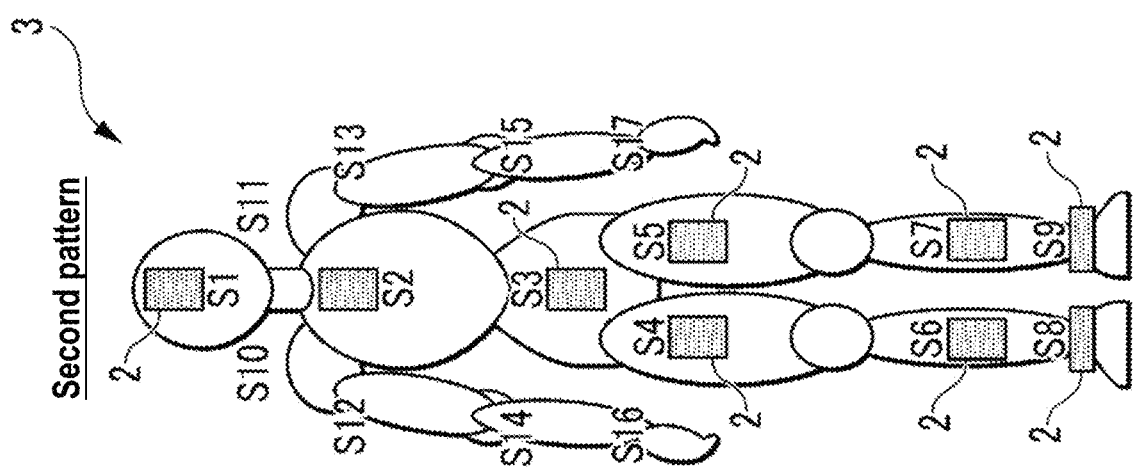

Further, as shown in FIG. 3, arrangement modes of second to k-th (=several hundreds) patterns are set. As shown in the drawing, the second pattern is a mode in which the inertial measurement unit sensor 2 is disposed in only segments S1 to S9, and the k-th pattern is a mode in which the inertial measurement unit sensor 2 is disposed in only the segments S4 to S9. The above-described first to k-th patterns are set to be disposed in segments S1 to S17 in different modes while appropriately selecting the inertial measurement unit sensors 2 within 1 to 17 ranges. That is, as an arrangement mode of the inertial measurement unit sensors 2, k patterns that are different from each other are set.

Next, after the inertial measurement unit sensors 2 are actually attached to a human in an arrangement mode of the above-described first pattern, a sampling process for detected signals of the inertial measurement unit sensors 2 is executed by the controller 10. Specifically, each of m predetermined actions from a first action to an m-th action is executed a predetermined number of times (for example, several tens of times) by a person, and detected signals of the inertial measurement unit sensors 2 in the meantime are sampled by the controller 10 at predetermined time intervals and written in the RAM. In this case, the first to m-th actions are executed as predetermined actions such as "sit", "stand up", "walk", . . . , and "throw".

Thereby, pieces of time-series data of detected signals indicating a three-axial acceleration, a three-axial rotation angle, and a three-axial terrestrial magnetism are acquired as raw data for creating a database, and these pieces of data are written in the RAM as a first database.

Subsequently, in the controller 10, arithmetic data such as a three-axial acceleration, a three-axial speed, a three-axial terrestrial magnetism, a three-axial rotation angle, or an attitude angle is calculated on the basis of raw data for creating a database, and these pieces of data are written in the RAM as a second database. This arithmetic data is also created for time-series data when any one of m predetermined actions is executed, similar to the raw data.

Further, in the controller 10, data defining an action type (for example, standing-up and lowering down) for each discrete time is created as a label database which is teacher data for time-series data when any one (for example, sitting) of m predetermined actions is executed on the basis of data of the first database and the second database.

Figure 4:
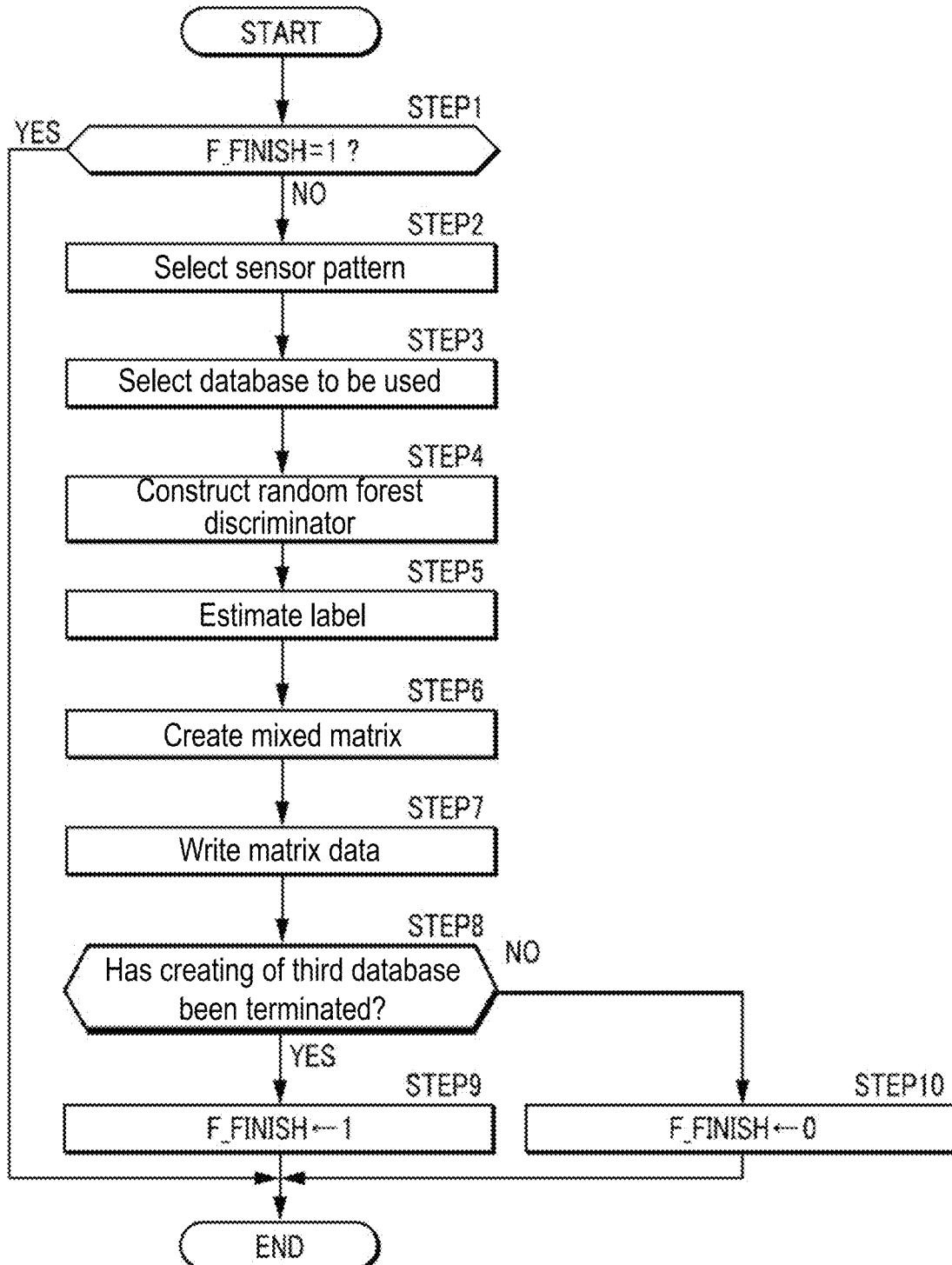
FIG. 4 is a flowchart showing a database creating process.

Next, a third database (see FIG. 7) is created through a database creating process shown in FIG. 4 using the first database, the second database, and the label database which are acquired as described above. The database creating process is executed at a predetermined control cycle by the controller 10.

As shown in the drawing, first, it is determined whether or not a database-created flag F_FINISH is "1" (FIG. 4/STEP1). The database-created flag F_FINISH indicates whether or not the third database has been created.

When a determination result is affirmative (FIG. 4/ STEP1 . . . YES), that is, when the third database has been created, this process is terminated as it is. On the other hand, when a determination result is negative (FIG. 4/STEP1 . . . NO), a sensor pattern selection process is executed (FIG. 4/STEP2).

In this process, as a sensor pattern, an i-th (i=1 to k) pattern is selected as an arrangement mode of the inertial measurement unit sensors 2. A value of 1 in this case is selected for each control cycle in the order of 1⇒ 2⇒ . . . ⇒k.

Subsequently, a use database selection process is executed (FIG. 4/STEP3). In this process, a first database and a second database are selected as follows as databases to be used in the present arithmetic operation in accordance with the sensor pattern selected in the above-described process.

Specifically, in a case where the sensor pattern is a pattern in which the inertial measurement unit sensors 2 are disposed to be continuously connected to respective segments (for example, a foot⇒a shin⇒a thigh⇒a waist, and the like), the first database and/or the second database is selected. On the other hand, in a case where the sensor pattern is a pattern in which the inertial measurement unit sensors 2 are disposed to be discontinuously connected to respective segments, the first database is selected.

Next, as described below, a random forest learning process is executed. In this process, a correct answer ratio of m predicted actions to m predetermined actions is calculated by a random forest method. The m predicted actions are equivalent to predicted values of the m predetermined actions. In addition, the correct answer ratio is equivalent to a ratio (probability) in which the m predetermined actions can be accurately detected when the test subject 3 executes the m predetermined actions from a first action to an m-th action, and is calculated as a value within a range from a value of 0 to a value of 1.

In this case, since the random forest method is well known, detailed description thereof will be omitted, but the random forest method is executed as follows. First, a random forest discriminator (predictor) is constructed (FIG. 4/STEP4). The random forest discriminator is constructed using a well-known method using the database and the label database which are selected as described above.

Subsequently, a label estimation process is executed (FIG. 4/STEP5). In the label estimation process, the estimation of a label is executed by applying new data having no label in a database to the random forest discriminator. Thereby, time-series data of a label is created as estimation results.

Next, a mixed matrix is created (FIG. 4/STEP6). Specifically, correct answer data of a label and estimation results are compared with each other, and a correct answer ratio of m predicted actions to any one predetermined action among m predetermined actions is calculated. In addition, correct answer ratios of all actions from a first action to an m-th action are calculated, and finally, m×m correct answer ratios are calculated. In addition, a mixed matrix is created using the m×m correct answer ratio.

Figure 5:
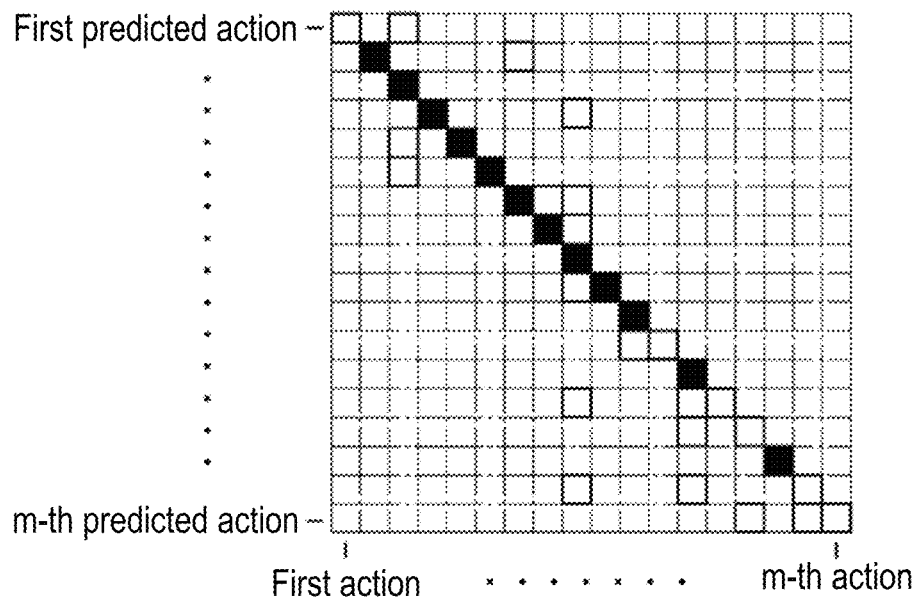
FIG. 5 is a diagram showing an example of calculation results of a mixed matrix of a first pattern.

In this case, for example, when m×m correct answer ratios are calculated in an arrangement mode of a first pattern, a mixed matrix shown in FIG. 5 is created. In the case of the mixed matrix, a vertical axis is set to be m predetermined actions from a first action to an m-th action, a horizontal axis is set to be m predicted actions from a first predicted action to an m-th predicted action, and a matrix having m×m correct answer ratios as elements is created.

Further, in the drawing, for ease of understanding, a correct answer ratio of each element in the mixed matrix is expressed by the shade of color, and is set to a value closer to a value of 1 as the color becomes darker. In other words, a correct answer ratio of each element is set to a value closer to a value of 0 as the color becomes lighter As it is apparent from FIG. 5, in the case of a mixed matrix, a correct answer ratio of a diagonal component is the highest. This is caused by the purpose of increasing prediction accuracy of the type of predicted action with respect to the type of predetermined action by a random forest method.

Figure 6:
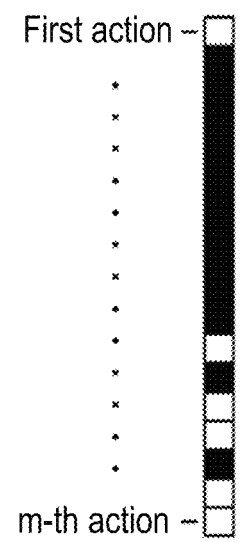
FIG. 6 is a diagram showing an example of calculation results of matrix data of a first pattern.

Subsequently, matrix data is written in the E2PROM 13 (FIG. 4/STEP7). The matrix data is data for creating a database and is configured as a matrix (vector) of m rows and one column with m diagonal components as elements in the above-described mixed matrix. That is, the matrix data is configured as a matrix with correct answer ratios in m predetermined actions from a first action to an m-th action as elements. For example, in the case of the mixed matrix shown in FIG. 5, matrix data shown in FIG. 6 is written in the E2PROM 13.

Subsequently, it is determined whether or not the creating of the third database has been terminated (FIG. 4/STEP8). In this case, it is determined that the creating of the third database has been terminated when the writing of matrix data in k arrangement modes from a first pattern to a k-th pattern has been terminated, and otherwise, it is determined that creating of the third database has not been terminated.

When a determination result is negative (FIG. 4/STEP8 . . . NO), that is, when the creating of the third database has not been terminated, the above-described database-created flag F_FINISH is set to "0" (FIG. 4/STEP10). Thereafter, this process is terminated.

On the other hand, when a determination result is affirmative (FIG. 4/STEP8 . . . YES), that is, when the creating of the third database has been terminated, the database-created flag F_FINISH is set to "1" in order to express the termination of the creating (FIG. 4/STEP9). Thereafter, this process is terminated.

Figure 7:
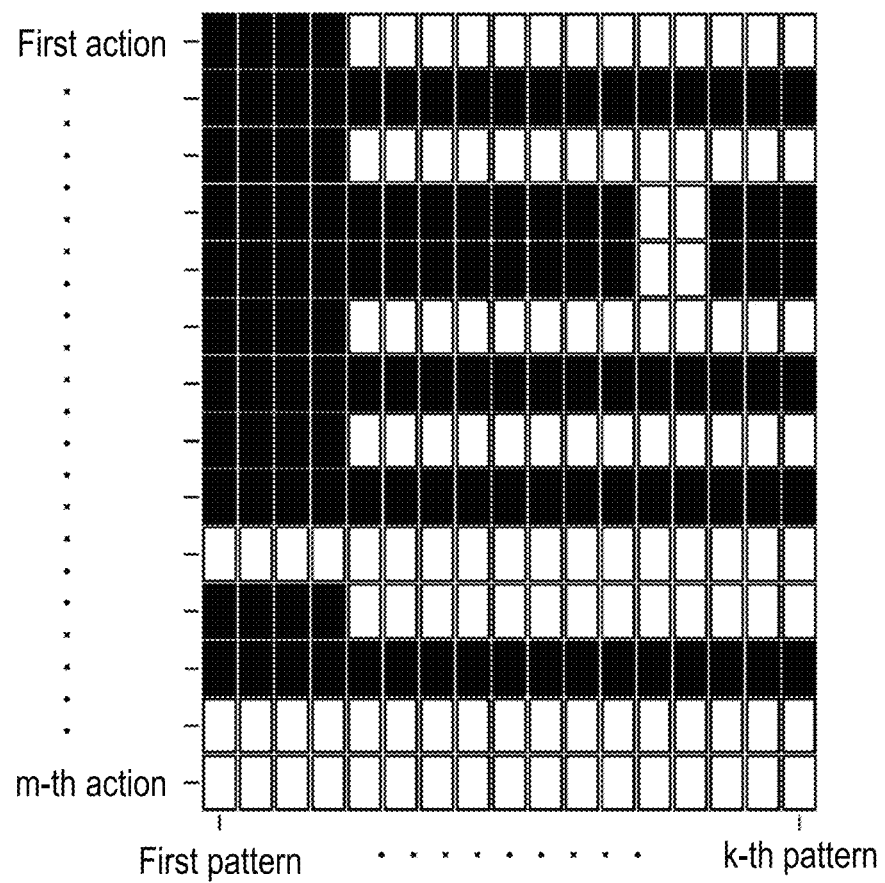
FIG. 7 is a diagram showing an example of calculation results of a third database.

As described above, the third database is created as shown in, for example, FIG. 7 by executing the database creating process in FIG. 4. The third databases are crated as databases defining a relationship between the k arrangement modes from the first pattern to the k-th pattern, the m predetermined actions from the first action to the m-th action, and the k×m correct answer ratios Next, an arrangement mode acquisition display process will be described with reference to FIG. 8. The arrangement mode acquisition display process is a process in which, when various conditions are selected by a user as will be described later, an arrangement mode of the inertial measurement unit sensors 2 corresponding thereto is acquired from a database and displayed on the display 11, and is executed at a predetermined control cycle by the controller 10.

Figure 8:
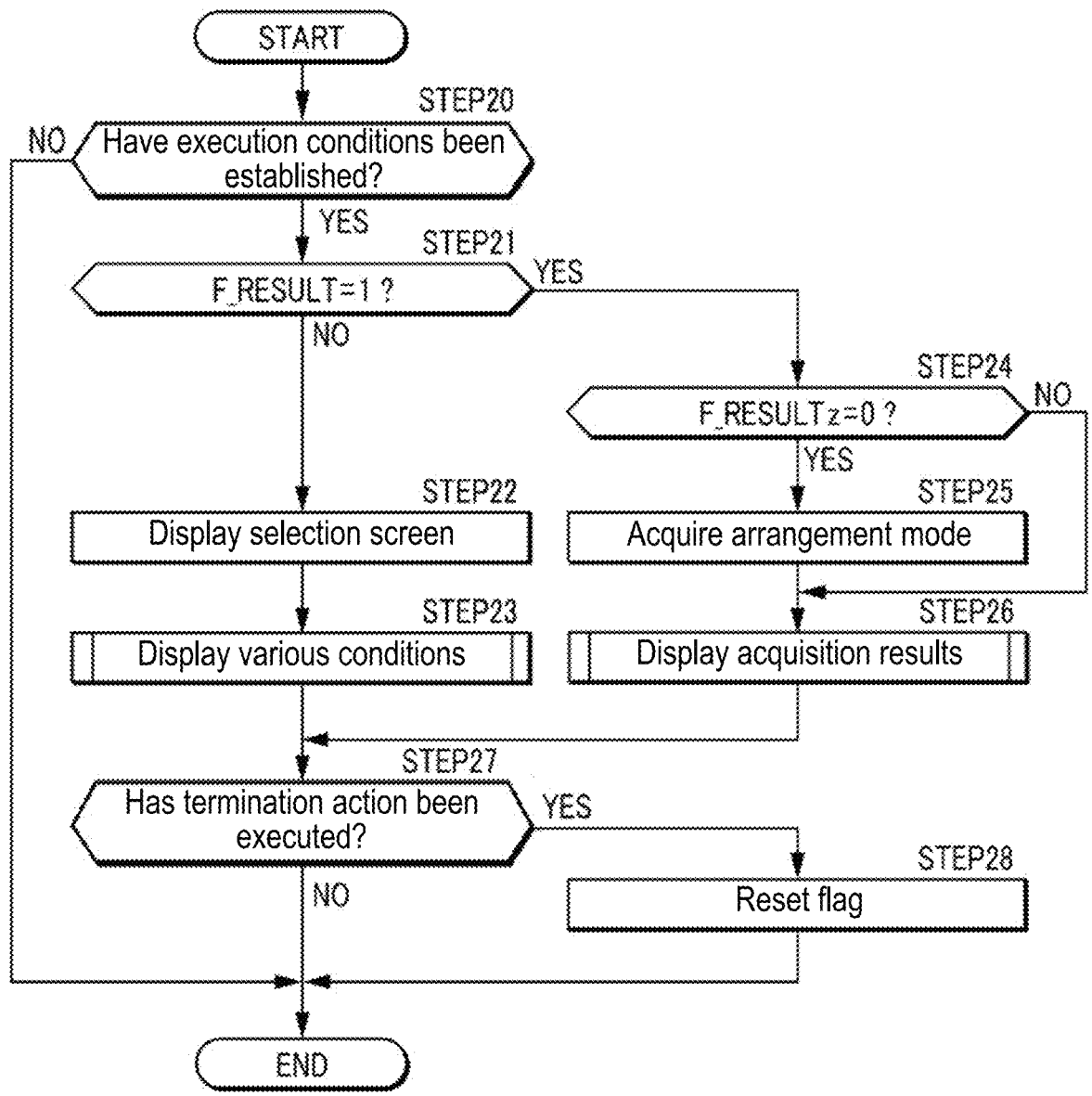
FIG. 8 is a flowchart showing an arrangement mode acquisition display process.

As shown in the drawing, first, it is determined whether or not execution conditions of the arrangement mode acquisition display process have been established (FIG. 8/STEP20). In this case, when a program of the arrangement mode acquisition display process is being executed, it is determined that execution conditions of the arrangement mode acquisition display process have been established, and otherwise, it is determined that execution conditions have not been established.

When a determination result is negative (FIG. 8/STEP20 . . . NO) and execution conditions of the arrangement mode acquisition display process have not been established, this process is terminated as it is.

On the other hand, when a determination result is affirmative (FIG. 8/STEP20 . . . YES) and execution conditions of the arrangement mode acquisition display process have been established, it is determined whether or not a result display flag F_RESULT is "1" (FIG. 8/STEP21). The result display flag F_RESULT indicates whether or not acquisition results of an arrangement mode should be displayed, and the value thereof is set as will be described later.

When a determination result is negative (FIG. 8/STEP21 . . . NO), a selection screen display process will be executed (FIG. 8/STEP22). In this process, for example, the selection screen 20 as shown in FIG. 11 is displayed on the display 11.

Hereinafter, the selection screen 20 will be described. As shown in the drawing, m check boxes 21 for selecting a predetermined action are displayed on the left end side of the selection screen 20 so as to be arranged in a line in a vertical direction at equal intervals. The m check boxes 21 are check boxes for respectively selecting m predetermined actions. In order to show this, each of the m predetermined actions such as "sit", "stand up", "walk", . . . , and "throw" is displayed side by side with each check box 21 on the right side of the m check boxes 21.

A user can select any action from the m predetermined actions or cancelling the selection by putting or removing a check mark with respect to the check boxes 21 through the input device 12. In addition, an all-cancellation button 22 and an all-selection button 23 are displayed side by side below the lowest check box 21. When the all-cancellation button 22 is pressed by the user operating the input device 12, a check mark is cancelled in all of the m check boxes 21. When the all-selection button 23 is pressed, a check mark is put in all of the m check boxes 21.

In addition, 17 check boxes 24 for selecting an attachment area are displayed on the right end of the check boxes 21 for selecting a predetermined action of the selection screen 20 so as to be arranged in a line in a vertical direction at equal intervals. The 17 check boxes 24 are check boxes for arbitrarily selecting an attachment area of the inertial measurement unit sensor 2 from 17 segments S1 to S17. In order to show this, each of specific names of "head", "chest", "waist", . . . , and "left hand" of the 17 segments S1 to S17 are displayed side by side with the respective check boxes 24 on the right side of the 17 check boxes 24.

The user can arbitrarily select an attachment area (disposition area) of the inertial measurement unit sensor 2 from the 17 segments S1 to S17 or can cancel the selection by putting or removing a check mark with respect to the check boxes 24 through the input device 12.

In addition, a display window 25 for an upper limit number of sensors is displayed below the lowest check box 24. The display window 25 displays an upper limit number of inertial measurement unit sensors 2 to be attached to the test subject 3 which is selected by the user, and an up button 25a and a down button 25b are displayed side by side in a vertical direction at the right end of the display window 25. When the up button 25a or the down button 25b is pressed, an upper limit number displayed on the display window 25 is changed between a value of 17 and a value of 1.

With the above-described configuration, the user can arbitrarily select an upper limit number of sensors between a value of 17 and a value of 1 while confirming the upper limit number of sensors on the display window 25 by pressing the up button 25a or the down button 25b through the input device 12.

Further, a result display button 27, a ranking display window 28, and a sensor combination display window 29 are displayed in order from the top to the bottom on the right side of the check boxes 24 for selecting an attachment area. Further, a result display window 30 is displayed on the right side of the button 27 and the windows 28 and 29.

The result display button 27 is a button for displaying acquisition results of an arrangement mode. When the result display button is pressed by the user through the input device 12, various pieces of data related to acquisition results of an arrangement mode are displayed on the ranking display window 28, the sensor combination display window 29, and the result display window 30 as will be described later.

The ranking display window 28 displays a numerical value indicating the ranking of a score of an arrangement mode of the inertial measurement unit sensors 2. Specifically, in the case of the ranking display window 28, when the above-described result display button 27 is pressed and an arrangement mode of the inertial measurement unit sensors 2 is acquired, a numerical value indicating the ranking of a score in acquisition results is displayed (see FIGS. 12 and 13 to be described later). The score is calculated as the sum of correct answer ratios in each of the acquired arrangement modes. Therefore, it can be expected that the higher the score of an arrangement mode, the higher the detection accuracy of one or more predetermined actions selected.

In the ranking display window 28, in a case where the result display button 27 is pressed, first, a numerical value 1 indicating that the score of an arrangement mode is a first rank is displayed (see FIGS. 12 and 13 to be described later). An up button 28a and a down button 28b are displayed side by side in a vertical direction at the right end of the ranking display window 28. The ranking of a score displayed on the ranking display window 28 is arbitrarily changed by pressing the up button 28a or the down button 28b.

With the above-described configuration, the user can arbitrarily select each ranking of a first rank or less as the ranking of a score displayed on the ranking display window 28 by pressing the up button 28a or the down button 28b through the input device 12.

In addition, a combination of attachment areas of the inertial measurement unit sensors 2 is displayed on the sensor combination display window 29 mentioned above. More specifically, in the case of the sensor combination display window 29, as shown in FIGS. 12 and 13 to be described later, when the ranking of a score is displayed on the ranking display window 28, a combination of attachment areas of the inertial measurement unit sensors 2 in an arrangement mode corresponding to the ranking is displayed in letters.

Further, an arrangement mode of the inertial measurement unit sensors 2 with respect to the test subject 3 and a score of each arrangement mode are displayed on the result display window 30. More specifically, as shown in FIGS. 12 and 13 to be described later, when the ranking of a score is displayed on the ranking display window 28, an arrangement mode of the inertial measurement unit sensors 2 corresponding to the ranking, and the like are displayed on the result display window 30.

In addition, an X button 31 is displayed at the upper right end of the selection screen 20. The X button 31 is a button for terminating the arrangement mode acquisition display process of FIG. 8, and the arrangement mode acquisition display process of FIG. 8 is terminated when the X button is pressed by the user operating the input device 12.

Referring back to FIG. 8, after the selection screen display process is executed as described above, a various-conditions display process is executed (FIG. 8/STEP23). In the various-conditions display process, selection states of various conditions by the user are displayed during the execution of the above-described selection screen display process, and details thereof will be described later.

On the other hand, when a result display flag F_RESULT is "1" (FIG. 8/STEP21 . . . YES) in a case where execution conditions of the above-described arrangement mode acquisition display process are established (FIG. 8/STEP20 . . . YES), it is determined whether or not a previous value F_RESULTz of a result display flag is "0" (FIG. 8/STEP24).

When a determination result is affirmative (FIG. 8/STEP24 . . . YES), that is, when the present control timing is a timing immediately after F_RESULT=1 is established, the arrangement mode acquisition display process is executed (FIG. 8/STEP25). In the arrangement mode acquisition display process, the above-described third database is retrieved in accordance with acquisition conditions (selection of an action, selection of an attachment area, an upper limit number of sensors) selected by the user in the above-described various-conditions display process, so that one or more arrangement modes corresponding to the acquisition conditions are acquired.

As described above, when the arrangement mode acquisition display process is executed or the above-described determination result is negative (FIG. 8/STEP24 . . . NO), an acquisition result display process is subsequently executed (FIG. 8/STEP26). In the acquisition result display process, an arrangement mode acquired in the above-described arrangement mode acquisition display process is displayed on the result display window 30 or the like, and details thereof will be described later.

After the above-described various-conditions display process or acquisition result display process is executed, it is determined whether or not a termination action has been executed (FIG. 8/STEP27). In this case, when the X button 31 of the selection screen 20 mentioned above is pressed by the user operating the input device 12, it is determined that a termination action has been executed, and otherwise, it is determined that a termination action has not been executed.

When a determination result is negative (FIG. 8/STEP27 . . . NO), this process is terminated as it is. On the other hand, when a determination result is affirmative (FIG. 8/STEP27 . . . YES), a flag reset process is executed (FIG. 8/STEP28), and then this process is terminated as it is. In the flag reset process, a result display flag F_RESULT, a ranking change flag F_CHANGE to be described later, a ranking change display flag F_DISPLAY to be described later, and the like are all reset to "0".

Next, the above-described various-conditions display process (FIG. 8/STEP23) will be described with reference to FIG. 9. The various-conditions display process is a process of displaying selection states of various conditions by a user as described below.

Figure 9:
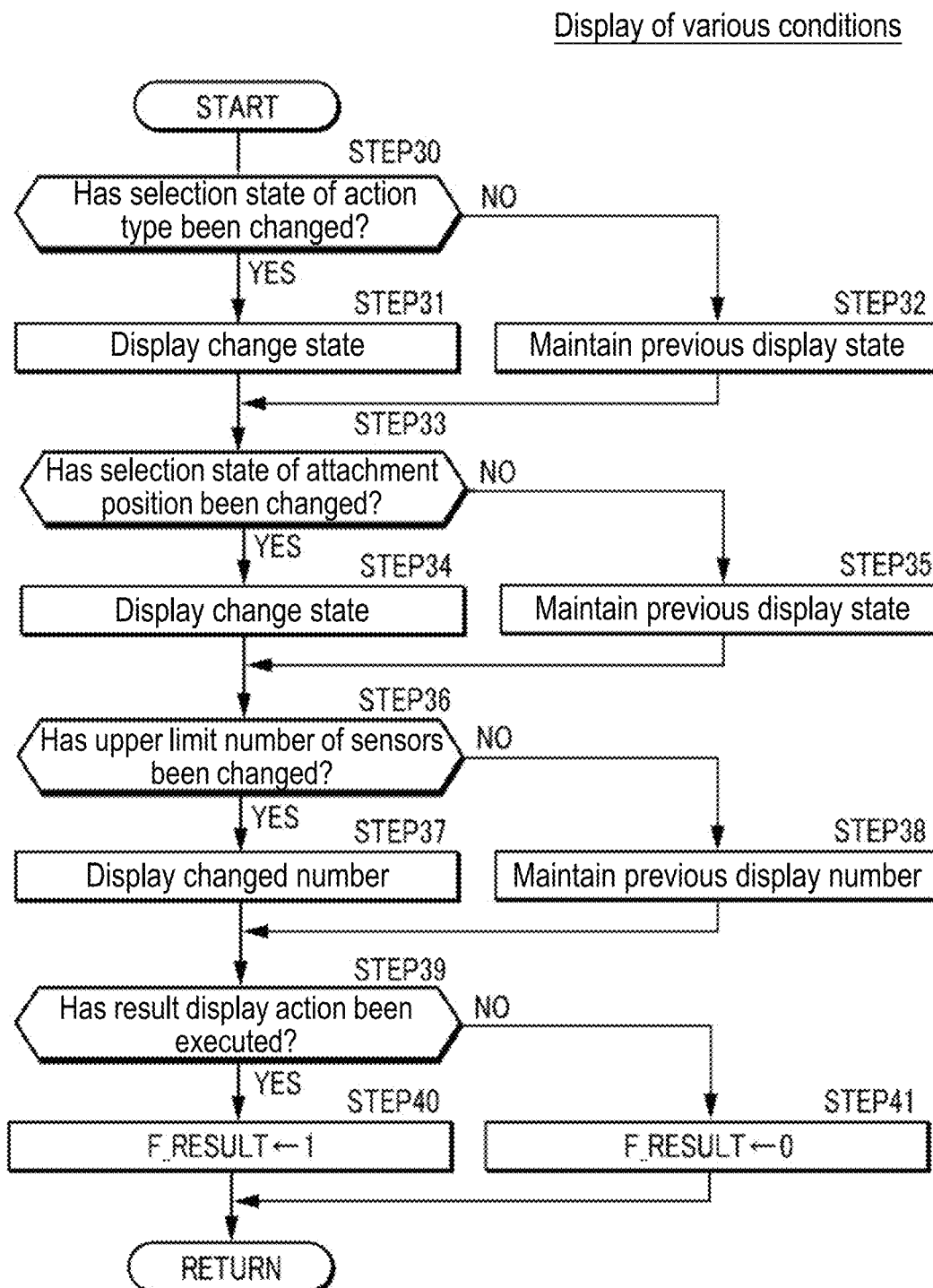
FIG. 9 is a flowchart showing a various-conditions display process.

As shown in the drawing, first, it is determined whether or not a selection state of an action type has been changed (FIG. 9/STEP30). In this case, when an action of changing the check marks in the check boxes 21 is executed by the user operating the input device 12, it is determined that a selection state of an action type has been changed, and otherwise, it is determined that selection state of an action type has not been changed.

When a determination result is affirmative (FIG. 9/STEP30 . . . YES), a change state of an action type is displayed (FIG. 9/STEP31). That is, a display state of a check mark in the check box 21 is changed. On the other hand, when a determination result is negative (FIG. 9/STEP30 . . . NO), a previous display state of an action type is maintained (FIG. 9/STEP32). That is, a display state of a check mark in the check box 21 is maintained.

As described above, after display change/display maintenance of an action type is executed, it is determined whether or not a selection state of an attachment position of the inertial measurement unit sensor 2 has been changed (FIG. 9/STEP33).

In this case, when an action of changing the check marks in the check boxes 24 is executed by the user operating the input device 12, it is determined that a selection state of an attachment position of the inertial measurement unit sensor 2 has been changed, and otherwise, it is determined that a selection state of an attachment position of the inertial measurement unit sensor 2 has not been changed.

When a determination result is affirmative (FIG. 9/STEP33 . . . YES), a change state of an attachment position is displayed (FIG. 9/STEP34). That is, a display state of a check mark in the check box 24 is changed. On the other hand, when a determination result is negative (FIG. 9/STEP33 . . . NO), a previous display state of an attachment position is maintained (FIG. 9/STEP35). That is, a display state of a check mark in the check box 24 is maintained.

As described above, after display change/display maintenance of an attachment position is executed, it is determined whether or not an upper limit number of sensors has been changed (FIG. 9/STEP36). That is, it is determined whether or not the above-described up button 25a and down button 25b have been pressed by the user operating the input device 12.

When a determination result is affirmative (FIG. 9/STEP36 . . . YES) and an upper limit number of sensors has been changed, the changed number is displayed on the display window 25 (FIG. 9/STEP37). On the other hand, when a determination result is negative (FIG. 9/STEP36 . . . NO) and an upper limit number of sensors has not been changed, the displayed previous upper limit number of sensors is maintained (FIG. 9/STEP38). That is, the displayed previous number is displayed on the display window 25 as it is.

As described above, after display change/display maintenance of an upper limit number of sensors is executed, it is determined whether or not a result display action has been executed (FIG. 9/STEP39). That is, it is determined whether or not the result display button 27 mentioned above has been pressed by the user operating the input device 12.

When a determination result is affirmative (FIG. 9/STEP39 . . . YES), it is determined that acquisition results of an arrangement mode should be displayed. In order to show this, a result display flag F_RESULT is set to "1" (FIG. 9/STEP40). Thereafter, this process is terminated.

On the other hand, when the above-described determination result is negative (FIG. 9/STEP39 . . . NO), it is determined that it is not necessary to display acquisition results of an arrangement mode of the inertial measurement unit sensors 2. In order to show this, a result display flag F_RESULT is set to "0" (FIG. 9/STEP41). Thereafter, this process is terminated. As described above, a various-conditions display process is executed.

Next, the above-described acquisition result display process (FIG. 8/STEP26) will be described with reference to FIG. 10. The acquisition result display process is a process of displaying an arrangement mode and the like acquired in the above-described arrangement mode acquisition display process as described below.

Figure 10:
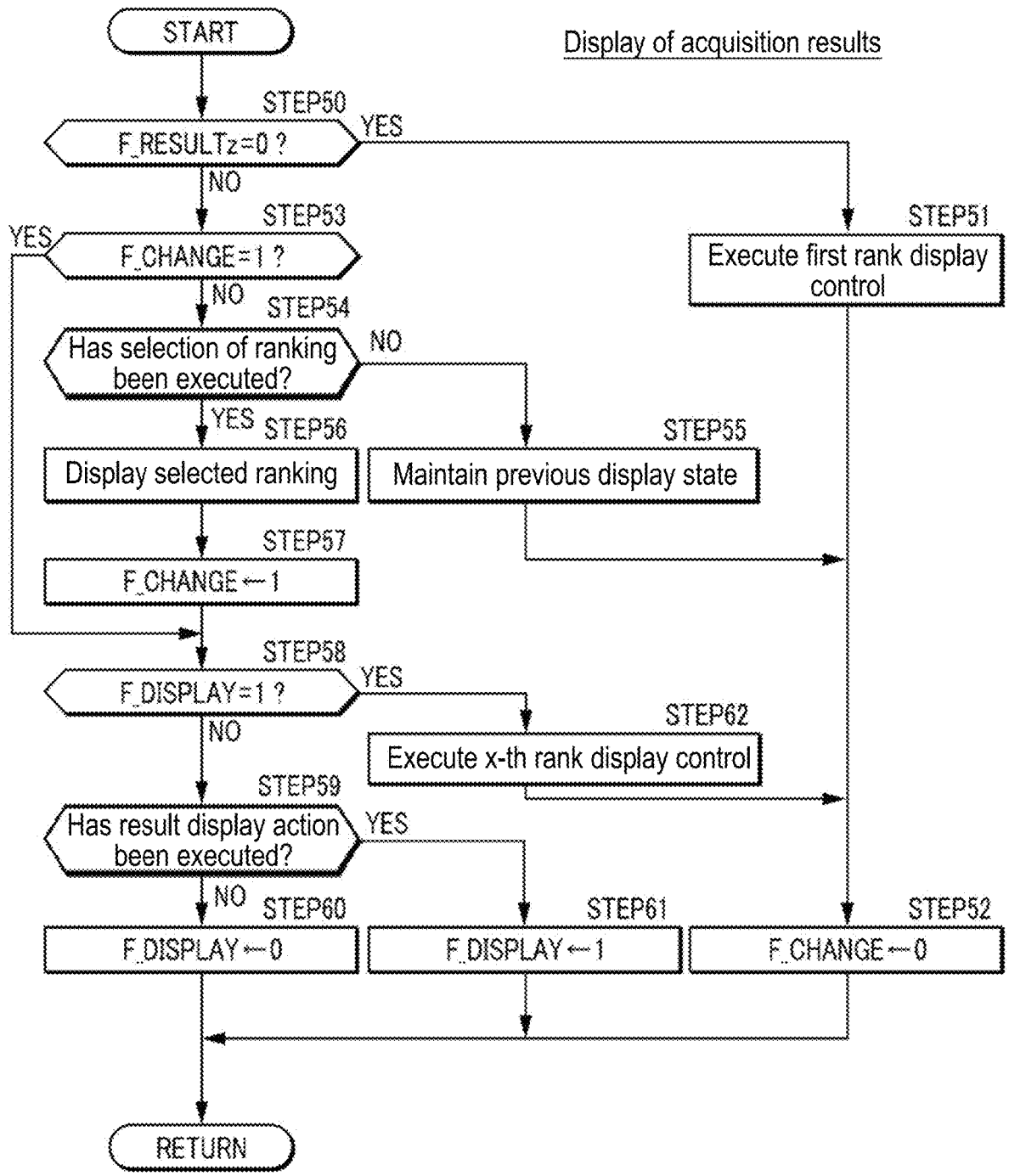
FIG. 10 is a flowchart showing an acquisition result display process.

As shown in the drawing, first, it is determined whether or not a previous value F_RESULTz of the above-described result display flag is "O" (FIG. 10/STEP50). When a determination result is affirmative (FIG. 10/STEP50 . . . YES), that is, when the present control timing is a timing immediately after F_RESULT=1 is established, a first rank display control process is executed (FIG. 10/STEP51).

Figure 12:
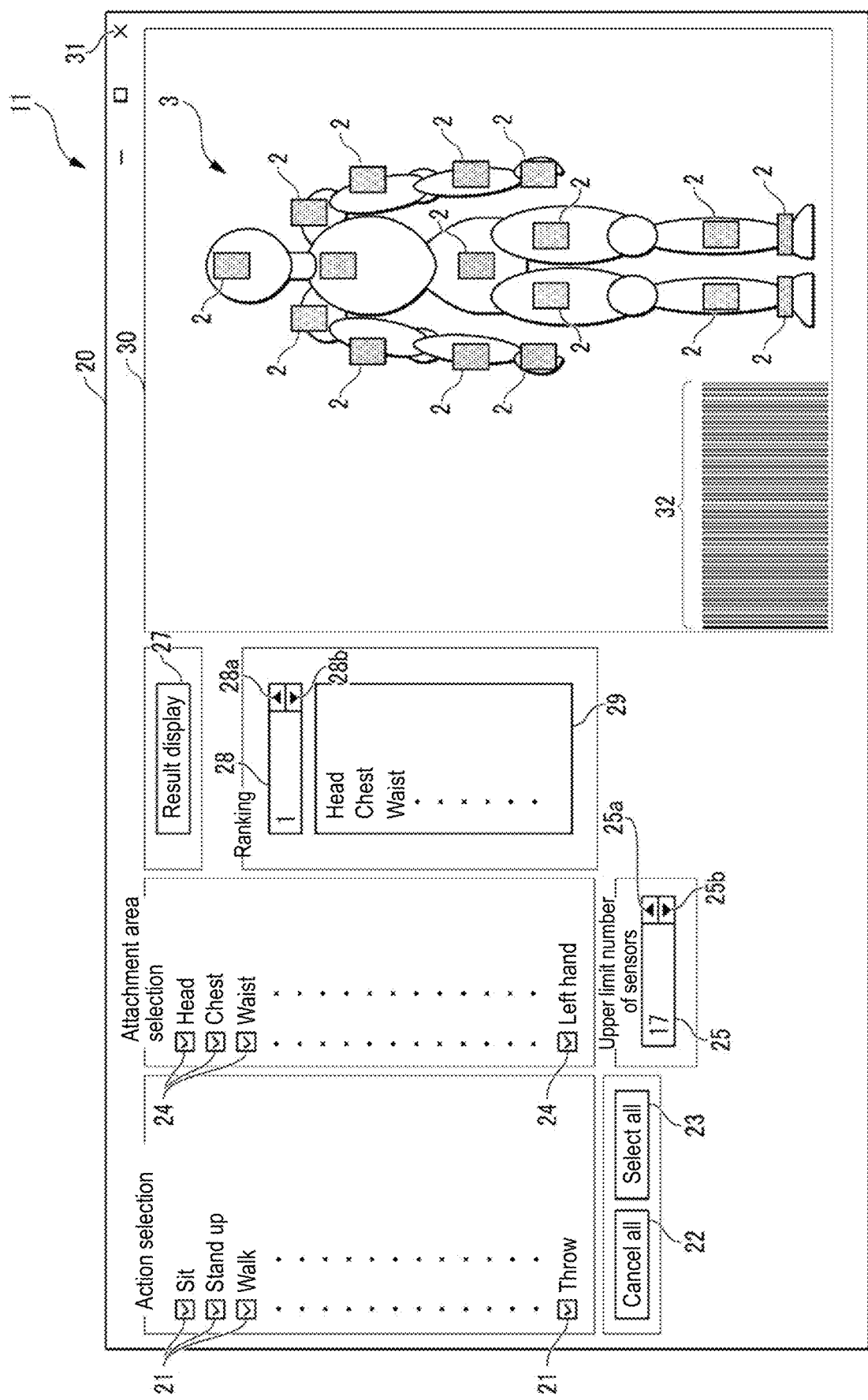
FIG. 12 is a diagram showing a display example of a selection screen and acquisition results.
Figure 13:
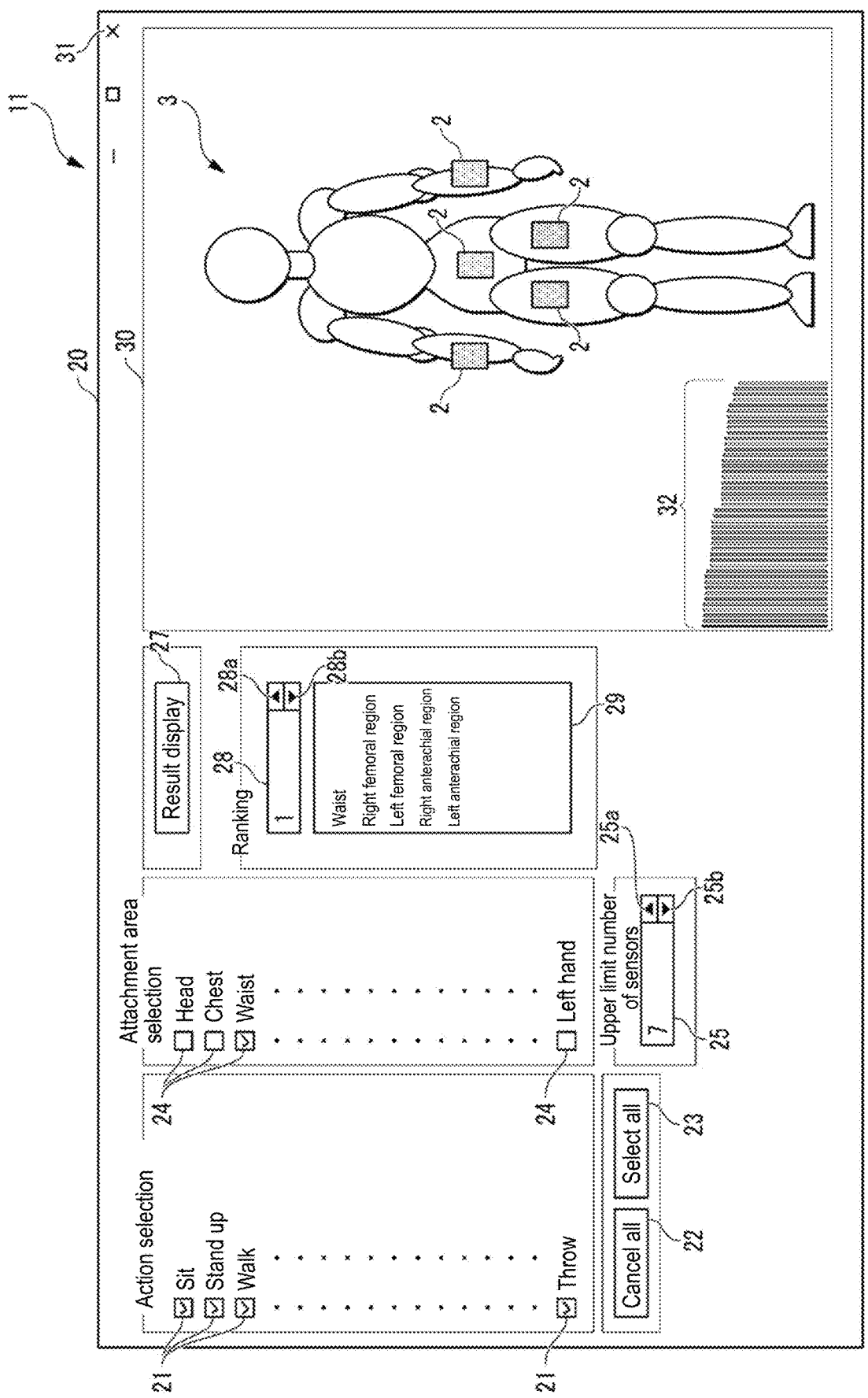
FIG. 13 is a diagram showing another display example of a selection screen and acquisition results.

In the first rank display control, as shown in FIG. 12 or FIG. 13, an arrangement mode of a score of a first rank among arrangement modes of the inertial measurement unit sensors 2 which are acquired in the arrangement mode acquisition display process is displayed on the result display window 30 so as to correspond to a segment of the test subject 3.

In this case, acquisition results of an arrangement mode shown in FIG. 12 are obtained when an upper limit number of sensors is set to be 17, m predetermined actions are all selected, and 17 attachment areas are all selected. In addition, acquisition results of an arrangement mode shown in FIG. 13 are obtained when an upper limit number of sensors is set to be 7, some of m predetermined actions are selected, and some of 17 attachment areas are selected.

Further, as shown in both the drawings, scores 32 of all acquired arrangement modes are displayed in the form of a bar graph in a lower left space of the result display window 30. More specifically, the scores 32 of all of the arrangement modes are displayed such that lower-ranked scores 32 are lined up from the left to the right with a score 32 at the left end as a first rank.

Further, in these scores 32, a score 32 corresponding to the ranking displayed on the ranking display window 28 is displayed in color darker than those of the other scores 32. In the case of both the drawings, a score of a first rank is displayed in color darker than those of the other scores 32. Further, a combination of attachment areas of sensors in an arrangement mode of the ranking is displayed in letters on the sensor combination display window 29.

As described above, after the first rank display control process is executed, a ranking change flag F_CHANGE is set to "0" (FIG. 10/STEP52). Thereafter, this process is terminated.

On the other hand, when the above-described determination result is negative (FIG. 10/STEP50 . . . NO), that is, F_RESULTz=1 is established and when an acquisition result display process is executed at a control timing prior to the previous control timing, it is determined whether or not a ranking change flag F_CHANGE is "1" (FIG. 10/STEP53). When a determination result is negative (FIG. 10/STEP53 . . . NO), it is determined whether or not the selection of a ranking has been executed (FIG. 10/STEP54).

In this case, when the up button 28a or the down button 28b of the ranking display window 28 mentioned above is pressed by the user operating the input device 12, it is determined that the selection of a ranking has been executed, and otherwise, it is determined that the selection of a ranking has not been executed. Meanwhile, also when the up button 28a is pressed in a state where a first rank is displayed on the ranking display window 28, it is determined that the selection of a ranking has not been executed.

When a determination result is negative (FIG. 10/STEP54 . . . NO), that is, the selection of a ranking has not been executed, a display state of the result display window 30 is maintained at a display state at the previous control timing (FIG. 10/STEP55). Subsequently, as described above, a ranking change flag F_CHANGE is set to "0" (FIG. 10/STEP52), and then this process is terminated.

On the other hand, when the above-described determination result is affirmative (FIG. 10/STEP54 . . . YES), that is, the selection of a ranking has been executed, a selected ranking display process is executed (FIG. 10/STEP56). In the selected ranking display process, a ranking selected by the user is displayed on the ranking display window 28.

Subsequently, in order to represent that the selection of a ranking has been executed by the user, the above-described ranking change flag F_CHANGE is set to "1" (FIG. 10/STEP57). When the ranking change flag F_CHANGE is set to "1" as described above or the above-described determination result is affirmative (FIG. 10/STEP53 . . . YES) and F_CHANGE=1 is established, it is subsequently determined whether or not the ranking change display flag F_DISPLAY is "1" (FIG. 10/STEP58).

When a determination result is negative (FIG. 10/STEP58 . . . NO), it is determined whether or not a result display action has been executed (FIG. 10/STEP59). That is, it is determined whether or not the result display button 27 has been pressed by the user operating the input device 12.

When a determination result is negative (FIG. 1O/STEP59 . . . NO), the ranking change display flag F_DISPLAY is set to "0" (FIG. 10/STEP60), and then this process is terminated. On the other hand, when a determination result is affirmative (FIG. 10/STEP59 . . . YES), the ranking change display flag F_DISPLAY is set to "1" (FIG.

10/STEP61) in order to represent that the result display button 27 has been pressed, and then this process is terminated.

In this manner, when the ranking change display flag F_DISPLAY is set to "1", the above-described determination result is affirmative (FIG. 10/STEP58 . . . YES). In this case, an X-th display control process is executed (FIG. 10/STEP62). In the X-th display control process, although not shown in the drawing, various pieces of data are displayed as described below. That is, an X-th (X is an integer) arrangement mode displayed on the ranking display window 28 is displayed on the result display window 30, an X-th score 32 among the scores 32 is displayed in color darker than those of the other scores 32. In addition, a combination of the inertial measurement unit sensors 2 in an X-th arrangement mode is displayed in letters on the sensor combination display window 29.

Subsequently, as described above, the ranking change flag F_CHANGE is set to "0" (FIG. 10/STEP52), and then this process is terminated.

As described above, according to the sensor arrangement mode acquisition device 1 of the embodiment, when the result display button 27 is pressed during the execution of an arrangement mode acquisition display process, one or more arrangement modes are acquired in association with the same number of scores as the number of arrangement modes by a user retrieving a first database or a second database in accordance with various selection states (selection states of an upper limit number of sensors, selection states of m predetermined actions or less among m predetermined actions, and selection states of attachment areas of the inertial measurement unit sensors 2).

In addition, when one or more arrangement modes are acquired, various acquisition results related to an arrangement mode are displayed on three display windows 28 to 30. That is, the ranking of a score of an arrangement mode of the inertial measurement unit sensors 2 is displayed on the ranking display window 28. In addition, a combination of attachment areas of the inertial measurement unit sensors 2 in the arrangement mode of the score of the ranking displayed on the ranking display window 28 is displayed in letters on the sensor combination display window 29. Further, the arrangement mode of the score of the ranking displayed on the ranking display window 28 is displayed on the result display window 30 in a state where the inertial measurement unit sensors 2 are associated with segments of the test subject 3.

In this case, the user can arbitrarily change a ranking to be displayed on the ranking display window 28 by pressing the up button 28a or the down button 28b through the input device 12, and thus it is possible to confirm an arrangement mode of a score of a changed ranking on the sensor combination display window 29 and the result display window 30 while changing a ranking of a score in this manner. In this case, a score of an arrangement mode indicates the level of detection accuracy of a predetermined action of an arrangement mode as described above, and thus the user can easily retrieve and acquire an optimal arrangement mode while evaluating a detection accuracy of a predetermined action highly required to be detected and an upper limit number of sensors.

In addition, as described above, one or more arrangement modes are acquired in accordance with selection states of attachment areas of the inertial measurement unit sensors 2, and thus the arrangement modes can be acquired in a state where a segment in which the inertial measurement unit sensor 2 cannot be disposed and a segment in which the inertial measurement unit sensor 2 is not desired to be disposed are excluded. Thereby, it is possible to improve user convenience.

Meanwhile, the embodiment is an example in which a human is used as a test subject. However, the test subject in the disclosure is not limited thereto, and anything that executes a personal action may be used. For example, a human with a humanoid robot or an assist robot mounted thereon may be used as a test subject. In addition, a human or a humanoid robot having some tool (for example, a bat or a racket) may be used as a test subject, and in this case, a sensor such as an inertial measurement unit sensor may be additionally disposed in the tool.

Further, when a database is created, a configuration in which a first database and a second database are created by attaching the inertial measurement unit sensor 2 to a humanoid robot instead of a human and then sampling a detected signal of the inertial measurement unit sensor 2 may be adopted.

In addition, the embodiment is an example in which the inertial measurement unit sensor 2 is used as a sensor. However, the sensor in the disclosure is not limited thereto, and anything capable of detecting a predetermined action of a test subject executing a personal action may be used. For example, a gyro sensor, an acceleration sensor, a power sensor, a biological sensor, or the like may be used as a sensor, or a combination of these sensors and an inertial measurement unit sensor may be used. In this case, a sensor having the same sampling rate may be used.

Further, the embodiment is an example in which 17 inertial measurement unit sensors 2 are used as n sensors. However, the number of sensors n in the disclosure is not limited thereto, and may be two or more. For example, the number of sensors n may be set to be a value 2 to 16 or a value of 18 or more.

On the other hand, the embodiment is an example in which one inertial measurement unit sensor 2 is disposed in one segment. However, an arrangement mode of sensors in the disclosure is not limited thereto, and a plurality of sensors may be disposed in one segment. Further, in a case where a single sensor includes a plurality of pieces of detection information, it is possible to obtain the same effects as in a case where a plurality of sensors are disposed in one segment.

In addition, the embodiment is an example in which an area of a test subject is divided into 17 segments, but a test subject may be divided into 16 or less segments or 18 or more segments.

Further, the embodiment is an example in which the number of arrangement modes of the inertial measurement unit sensors 2 is set to be k (k is several hundreds), but the value of k may be two or more. For example, the value of k may be set to be a value within a range from a value of 2 to a value of less than several hundreds or a value within a range exceeding several hundreds.

On the other hand, the embodiment is an example in which the number of predetermined actions of a test subject is set to m (m is several tens), but the value of m may be two or more. For example, the value of m may be set to be a value within a range from a value of 2 to less than several tens or a value within a range exceeding several tens.

In addition, the embodiment is an example in which a correct answer ratio is used as a prediction accuracy parameter. However, the prediction accuracy parameter in the disclosure is not limited thereto, and may indicate prediction accuracy of detection results of m predetermined actions of a test subject. For example, a value obtained by converting a correct answer ratio into a percentage may be used as the prediction accuracy parameter.

Further, the embodiment is an example in which the E2PROM 13 is used as a database storage part. However, the database storage part in the disclosure is not limited thereto, and may be a part that can store a database. For example, a ROM or a RAM may be used as the database storage part.

On the other hand, the embodiment is an example of a configuration in which 17 check boxes 24 for selecting an attachment area are provided, and attachment areas of the inertial measurement unit sensors 2 are selected through the check boxes, but a configuration in which 17 check boxes 24 for selecting an attachment area are omitted, and the selection of attachment areas of the inertial measurement unit sensors 2 is not executed may be adopted.

In addition, the embodiment is an example in which a plurality of scores 32 are displayed in the form of a bar graph, but the plurality of scores 32 may be displayed in the form of any graph other than a bar graph. For example, a plurality of scores 32 may be displayed in the form of a graph of broken line.

Further, the embodiment is an example of a configuration in which a user can select and display any arrangement mode between an arrangement mode of a highest score 32 and an arrangement mode of a lowest score 32 among acquisition results of arrangement modes by the user operating the up button 28*a* and the down button 28*b* through the input device 12, but a configuration in which arrangement modes to be displayed are automatically switched and displayed at predetermined time intervals in order of the level of prediction accuracy may be adopted.

On the other hand, the embodiment is an example in which the input device 12 constituted by a keyboard and a mouse is used, and alternatively, a touch panel type input device, an input device capable of inputting a gesture or a sound as an input signal, or the like may be used.

In addition, the embodiment is an example in which a random forest is used as a predetermined machine learning method. However, the predetermined machine learning method in the disclosure is not limited thereto, and anything capable of calculating k×m prediction accuracy parameters may be used. For example, a deep reinforcement learning method such as DQN (deep Q-network) may be used as a predetermined machine learning method.

Further, the embodiment is an example in which an arrangement mode acquired by the controller 10 is displayed on the display 11, and alternatively, a configuration in which an arrangement mode acquired by the controller 10 is printed on paper or the like or output in a format of a sound from a speaker or the like may be adopted. In this case, a sensor arrangement mode may be evaluated with reference to printing results or by listening to sound outputs.

According to the sensor arrangement mode acquisition device, in a case where the first predetermined number of sensors is selected by the number-of-sensors selection part and the second predetermined number of actions are selected by the predetermined action selection part, one or more arrangement modes according to the number of sensors within a range of the first predetermined number or less are acquired from the predetermined database in association with the second predetermined number of prediction accuracy parameters according to the second predetermined number of actions. Thereby, the one or more arrangement modes acquired in this manner are displayed on, for example, a display device or printed on paper, so that a user can easily acquire an optimal arrangement mode while evaluating a detection accuracy of a predetermined action highly required to be detected and a limitation on the number of sensors.

Further, in this case, the predetermined database defines a relationship between k×m prediction accuracy parameters indicating prediction accuracies of detection results of m predetermined actions of the test subject when the sensors are disposed in the test subject in k different arrangement modes in each of which the number of sensors within a range of n or less is disposed, k arrangement modes of n sensors or less, and m predetermined actions. Therefore, the user can appropriately acquire the above-described optimal arrangement mode from all of the k arrangement modes.

In the disclosure, it is preferable that the sensor arrangement mode acquisition device further include a segment selection part (input device 12) for selecting a segment in which a sensor is disposed among a plurality of the segments in a case where the test subject is divided into a plurality of segments, in which the arrangement mode acquisition part acquires the number of sensors within a range of the first predetermined number or less and the one or more arrangement modes according to the segments in which the sensors are disposed from the predetermined database in association with the second predetermined number of prediction accuracy parameters according to the second predetermined number of actions when the segment for disposing the sensor is selected by the segment selection part in a case where the first predetermined number of sensors and the second predetermined number of actions are selected.

According to the sensor arrangement mode acquisition device, one or more arrangement modes are acquired in accordance with selection states of segments in which the sensors are disposed in addition to the selection of the first predetermined number of sensors and the second predetermined number of actions, and thus the one or more arrangement modes can be acquired in a state where a segment in which a sensor cannot be disposed and a segment in which a sensor is not desired to be disposed are excluded. Thereby, it is possible to improve user convenience.

In the disclosure, it is preferable that the sensor arrangement mode acquisition device further include an arrangement mode display part (display 11) which displays the one or more arrangement modes in order on the basis of the levels of the prediction accuracies indicated by the second predetermined number of prediction accuracy parameters associated with each of the one or more arrangement modes in a case where the one or more arrangement modes are acquired by the arrangement mode acquisition part.

According to the sensor arrangement mode acquisition device, in a case where one or more arrangement modes are acquired by the arrangement mode acquisition part, the one or more arrangement modes are displayed in order by the arrangement mode display part on the basis of the levels of the prediction accuracies indicated by the second predetermined number of prediction accuracy parameters associated with each of the one or more arrangement modes. Thereby, the user can search for an optimal arrangement mode while referring to a prediction accuracy and a change in an arrangement mode of the sensors. As a result, the user can easily and accurately acquire the optimal arrangement mode.

In the disclosure, it is preferable that the arrangement mode display part display the one or more arrangement modes in a state where the sensors are associated with a plurality of segments S1 to S17 when the test subject is divided into a plurality of segments.

According to the sensor arrangement mode acquisition device, the user can refer to the one or more arrangement modes in a state where the sensors are associated with a plurality of segments when the test subject is divided into a plurality of segments. Thereby, it is possible to further improve user convenience.

In the disclosure, it is preferable that the arrangement mode display part display levels of the prediction accuracies indicated by the second predetermined number of prediction accuracy parameters in a form of a graph.

According to the sensor arrangement mode acquisition device, the levels of the prediction accuracies indicated by the second predetermined number of prediction accuracy parameters are displayed in the form of a graph, and thus the user can more easily check the levels of the prediction accuracies between the arrangement modes. Thereby, the user can further easily acquire an optimal arrangement mode.

In the disclosure, it is preferable that the sensor arrangement mode acquisition device further include an arrangement mode selection part (input device 12) for selecting the arrangement mode in which the prediction accuracy has a predetermined ranking among the one or more arrangement modes in a case where the one or more arrangement modes are acquired, in which the arrangement mode display part displays the arrangement mode of the predetermined ranking in a case where the arrangement mode of the predetermined ranking is selected by the arrangement mode selection part.

According to the sensor arrangement mode acquisition device, an arrangement mode of a predetermined ranking can be arbitrarily selected and displayed, and thus the user can refer to the number of sensors and an arrangement mode while arbitrarily changing the ranking of an arrangement mode.

In another embodiment, it is preferable that the sensor arrangement mode acquisition method further include displaying the one or more arrangement modes in order on the basis of levels of the prediction accuracies indicated by the second predetermined number of prediction accuracy parameters associated with each of the one or more arrangement modes in a case where the one or more arrangement modes are acquired.

In the another embodiment, it is preferable that the one or more arrangement modes be displayed in a state where the sensors are associated with a plurality of segments when the test subject is divided into a plurality of segments.

In the disclosure, it is preferable that levels of the prediction accuracies indicated by the second predetermined number of prediction accuracy parameters be displayed in a form of a graph.

In the another embodiment, it is preferable that the sensor arrangement mode acquisition method further include selecting the arrangement mode in which the prediction accuracy has a predetermined ranking among the one or more arrangement modes in a case where the one or more arrangement modes are acquired, and displaying the arrangement mode of the predetermined ranking.

In the another embodiment, it is preferable that detected signals of the sensors when one subject out of a human and a humanoid robot executes the m predetermined actions be sampled in a state where the number of sensors within a range of n or less is disposed in the one subject in the k arrangement modes, the k×m prediction accuracy parameters be calculated by applying the sampled detected signals to a predetermined machine learning method, and the predetermined database be created by associating the k×m prediction accuracy parameters, the k arrangement modes, and the m predetermined actions with each other.

According to the sensor arrangement mode acquisition method, a predetermined database is created by associating k×m prediction accuracy parameters, k arrangement modes, and m predetermined actions with each other. In this case, the k×m prediction accuracy parameters are calculated by applying a sampled detected signal to a predetermined machine learning method, and thus the predetermined database can be easily created.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A sensor arrangement mode acquisition device that acquires arrangement modes of n sensors with respect to a test subject when m predetermined actions of the test subject executing a personal action are detected, wherein n is two or more, m is two or more, the sensor arrangement mode acquisition device comprising:
   a database storage part which stores a predetermined database defining a relationship among k×m prediction accuracy parameters indicating prediction accuracies of detection results of the m predetermined actions of the test subject when the sensors are disposed in the test subject in k different arrangement modes in each of which the number of sensors within a range of n or less is disposed, the k arrangement modes of the n or less sensors, and the m predetermined actions, wherein k is two or more;
   a number-of-sensors selection part for selecting a first predetermined number of sensors equal to or less than the n sensors from among the n sensors;
   a predetermined action selection part for selecting a second predetermined number of actions equal to or less than the m actions from among the m predetermined actions; and
   an arrangement mode acquisition part which acquires one or more arrangement modes according to the number of sensors within a range of the first predetermined number or less from the predetermined database associated with the second predetermined number of prediction accuracy parameters according to the second predetermined number of actions in a case where the first predetermined number of sensors is selected by the number-of-sensors selection part and the second predetermined number of actions is selected by the predetermined action selection part.

2. The sensor arrangement mode acquisition device according to claim 1, further comprising:
   a segment selection part for selecting a segment in which the sensor is disposed among a plurality of the segments in a case where the test subject is divided into a plurality of segments,
   wherein the arrangement mode acquisition part acquires the number of sensors within a range of the first predetermined number or less and the one or more arrangement modes according to the segments in which the sensors are disposed from the predetermined database associated with the second predetermined number of prediction accuracy parameters according to the second predetermined number of actions when the segment for disposing the sensor is selected by the segment selection part in a case where the first predetermined number of sensors and the second predetermined number of actions are selected.

3. The sensor arrangement mode acquisition device according to claim 1, further comprising:
an arrangement mode display part which displays the one or more arrangement modes in order on the basis of levels of the prediction accuracies indicated by the second predetermined number of prediction accuracy parameters that are associated with each of the one or more arrangement modes in a case where the one or more arrangement modes are acquired by the arrangement mode acquisition part.

4. The sensor arrangement mode acquisition device according to claim 3, wherein the arrangement mode display part displays the one or more arrangement modes in a state where the sensors are associated with a plurality of segments when the test subject is divided into a plurality of segments.

5. The sensor arrangement mode acquisition device according to claim 3, wherein the arrangement mode display part displays the levels of the prediction accuracies indicated by the second predetermined number of prediction accuracy parameters in a form of a graph.

6. The sensor arrangement mode acquisition device according to claim 3, further comprising:
an arrangement mode selection part for selecting the arrangement mode in which the prediction accuracy has a predetermined ranking among the one or more arrangement modes in a case where the one or more arrangement modes are acquired,
wherein the arrangement mode display part displays the arrangement mode of the predetermined ranking in a case where the arrangement mode of the predetermined ranking is selected by the arrangement mode selection part.

7. A sensor arrangement mode acquisition method of acquiring arrangement modes of n sensors with respect to a test subject when m predetermined actions of the test subject executing a personal action are detected, wherein n is two or more, m is two or more, the sensor arrangement mode acquisition method comprising:
storing a predetermined database defining a relationship among k×m prediction accuracy parameters indicating prediction accuracies of detection results of the m predetermined actions of the test subject when the sensors are disposed in the test subject in k different arrangement modes in each of which the number of sensors within a range of n or less is disposed, the k arrangement modes of the n or less sensors, and the m predetermined actions, wherein k is two or more;
selecting a first predetermined number of sensors equal to or less than the n sensors from among the n sensors;
selecting a second predetermined number of actions equal to or less than the m actions from among the m predetermined actions; and
acquiring one or more arrangement modes according to the number of sensors within a range of the first predetermined number or less from the predetermined database associated with the second predetermined number of prediction accuracy parameters according to the second predetermined number of actions in a case where the first predetermined number of sensors are selected and the second predetermined number of actions are selected.

8. The sensor arrangement mode acquisition method according to claim 7, further comprising:
selecting a segment in which the sensor is disposed among a plurality of the segments in a case where the test subject is divided into a plurality of segments; and
acquiring the number of sensors within a range of the first predetermined number or less and the one or more arrangement modes according to the segments in which the sensors are disposed from the predetermined database associated with the second predetermined number of prediction accuracy parameters according to the second predetermined number of actions when the segment for disposing the sensor is selected in a case where the first predetermined number of sensors and the second predetermined number of actions are selected.

9. The sensor arrangement mode acquisition method according to claim 7, further comprising:
displaying the one or more arrangement modes in order on the basis of levels of the prediction accuracies indicated by the second predetermined number of prediction accuracy parameters that are associated with each of the one or more arrangement modes in a case where the one or more arrangement modes are acquired.

10. The sensor arrangement mode acquisition method according to claim 9, wherein the one or more arrangement modes are displayed in a state where the sensors are associated with a plurality of segments when the test subject is divided into a plurality of segments.

11. The sensor arrangement mode acquisition method according to claim 9, wherein the levels of the prediction accuracies indicated by the second predetermined number of prediction accuracy parameters are displayed in a form of a graph.

12. The sensor arrangement mode acquisition method according to claim 9, further comprising:
selecting the arrangement mode in which the prediction accuracy has a predetermined ranking among the one or more arrangement modes in a case where the one or more arrangement modes are acquired; and
displaying the arrangement mode of the predetermined ranking.

13. The sensor arrangement mode acquisition method according to claim 7, wherein
detected signals of the sensors when one subject out of a human and a humanoid robot executes the m predetermined actions are sampled in a state where the number of sensors within a range of n or less is disposed in the one subject in the k arrangement modes,
the k×m prediction accuracy parameters are calculated by applying the sampled detected signals to a predetermined machine learning method, and
the predetermined database is created by associating the k×m prediction accuracy parameters, the k arrangement modes, and the m predetermined actions with each other.

* * * * *